United States Patent
Tonomura et al.

(10) Patent No.: US 10,266,555 B1
(45) Date of Patent: Apr. 23, 2019

(54) POLYCYCLIC AMINOSILANE COMPOUNDS AND MAKING METHOD

(71) Applicant: Shin-Etsu Chemical Co., Ltd., Tokyo (JP)

(72) Inventors: Yoichi Tonomura, Joetsu (JP); Tohru Kubota, Joetsu (JP); Takayuki Honma, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/167,978

(22) Filed: Oct. 23, 2018

(30) Foreign Application Priority Data

Oct. 24, 2017 (JP) .................................. 2017-204952

(51) Int. Cl.
C07F 7/18 (2006.01)

(52) U.S. Cl.
CPC .......... *C07F 7/1888* (2013.01); *C07F 7/1804* (2013.01)

(58) Field of Classification Search
None
See application file for complete search history.

(56) References Cited

U.S. PATENT DOCUMENTS 8,049,027 B2   11/2011  Honma et al.

FOREIGN PATENT DOCUMENTS

| JP | 2010-120925 A | 6/2010 |
| JP | 2010-285406 A | 12/2010 |
| JP | 2014-1152 A | 1/2014 |

*Primary Examiner* — Clinton A Brooks
(74) *Attorney, Agent, or Firm* — Birch, Stewart, Kolasch & Birch, LLP

(57) ABSTRACT

Polycyclic aminosilane compounds of specific structure are fully effective for use as silane coupling agents, surface treating agents, resin additives, paint additives, and adhesives and evolve little or no low-boiling alcohols during service.

4 Claims, 6 Drawing Sheets

POLYCYCLIC AMINOSILANE COMPOUNDS AND MAKING METHOD

CROSS-REFERENCE TO RELATED APPLICATION

This non-provisional application claims priority under 35 U.S.C. § 119(a) on Patent Application No. 2017-204952 filed in Japan on Oct. 24, 2017, the entire contents of which are hereby incorporated by reference.

TECHNICAL FIELD

This invention relates to polycyclic aminosilane compounds and a method for preparing the same. The polycyclic aminosilane compounds are useful as silane coupling agents, surface treating agents, resin additives, paint additives, and adhesives.

BACKGROUND ART

Silane compounds having an amino group are useful as silane coupling agents, surface treating agents, resin additives, paint additives, and adhesives. Known silane compounds having an amino group include organoxysilane compounds having a primary amino group such as aminopropyltrimethoxysilane, organoxysilane compounds having a secondary amino group such as N-phenylaminopropyltrimethoxysilane, and organoxysilane compounds having a tertiary amino group such as dimethylaminopropyltrimethoxysilane.

These silane compounds have only one functional or amino group per molecule. For this reason, they sometimes insufficiently develop effects due to functionality introduction when used as silane coupling agents, surface treating agents, resin additives, paint additives, and adhesives.

To solve the outstanding problem, Patent Documents 1 and 3 propose tertiary aminosilane compounds having an intramolecular organoxysilyl group and Patent Document 2 discloses a secondary aminosilane compounds having an intramolecular organoxysilyl group. Since these compounds react with moisture to form a hydroxyl group in addition to the original amino group, the effects due to functionality introduction become greater. These compounds are also regarded as less environmental load-providing compounds because the intramolecular organoxy moiety does not form low-boiling alcohols such as methanol and ethanol upon reaction with moisture.

CITATION LIST

Patent Document 1: JP-A 2010-120925
Patent Document 2: JP-A 2010-285406
Patent Document 3: JP-A 2014-001152

DISCLOSURE OF INVENTION

In the current applications of silane compounds including silane coupling agents, surface treating agents, resin additives, paint additives, and adhesives, silane compounds capable of exerting greater additive effects are required in compliance with the diversification of the intended purpose. In this context, the compounds of Patent Documents 1 to 3, which possess per molecule one amino group and one hydroxyl group resulting from reaction with moisture, exert rather less additive effects.

In conjunction with environmental problems deeply related to the global greenhouse effects and health impacts, one of the important themes is a saving of volatile organic compounds. Engineers made efforts to achieve a saving of volatile organic compounds by reducing the amount of low-boiling alcohols evolving from organoxysilane compounds. There is a desire to have a silane compound evolving a smaller amount of low-boiling alcohol.

An object of the invention is to provide a silane compound which exerts greater additive effects when used as silane coupling agents, surface treating agents, resin additives, paint additives, and adhesives, and which evolves a minimal amount of low-boiling alcohol, and a method for preparing the same.

The inventors have found that a polycyclic aminosilane compound of specific structure exerts greater additive effects when used as silane coupling agents, surface treating agents, resin additives, paint additives, and adhesives, and evolves little or no low-boiling alcohol.

In one aspect, the invention provides a polycyclic aminosilane compound having the general formula (1).

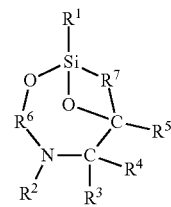

(1)

Herein $R^1$ is a substituted or unsubstituted $C_1$-$C_{20}$ monovalent hydrocarbon group or an organoxy group having the general formula (2):

$$-OR^8 \quad (2)$$

wherein $R^8$ is a substituted or unsubstituted $C_1$-$C_{20}$ monovalent hydrocarbon group. $R^2$ to $R^5$ are each independently a substituted or unsubstituted $C_1$-$C_{20}$ monovalent hydrocarbon group. $R^6$ and $R^7$ are each independently a substituted or unsubstituted $C_1$-$C_{20}$ divalent hydrocarbon group which may contain a heteroatom.

In another aspect, the invention provides a method for preparing the polycyclic aminosilane compound defined above, comprising the steps of reacting an epoxy-containing organoxysilane compound having the general formula (3) with a hydroxyl-containing amine compound having the general formula (4), and distilling the resulting reaction mixture.

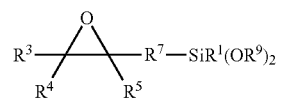

(3)

Herein $R^1$, $R^3$, $R^4$, $R^5$ and $R^7$ are as defined above, $R^9$ is a substituted or unsubstituted $C_1$-$C_{20}$ monovalent hydrocarbon group.

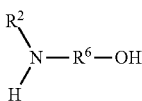

(4)

Herein $R^2$ and $R^6$ are as defined above.

Preferably, the distilling step is carried out in the presence of a basic catalyst or acid catalyst. Also preferably, in the distilling step, a compound having a higher boiling point than the polycyclic aminosilane compound of formula (1) is used as a solvent.

Advantageous Effects of Invention

The polycyclic aminosilane compounds of the invention exert great additive effects and evolve little or no low-boiling alcohols during service. They are useful as silane coupling agents, surface treating agents, resin additives, paint additives, and adhesives.

DESCRIPTION OF PREFERRED EMBODIMENTS

Figure 1:
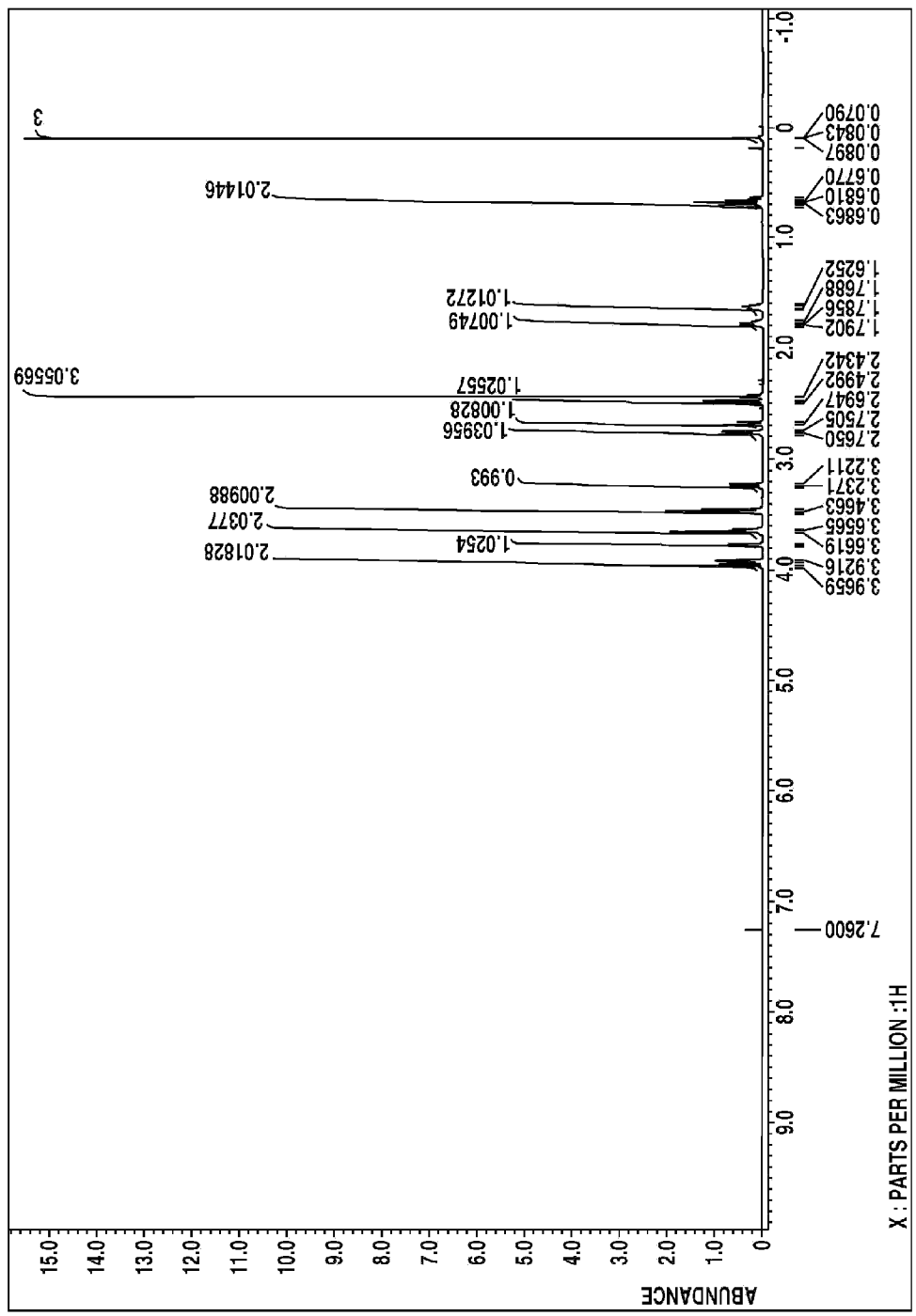
FIGS. 1 and 2 are diagrams showing $^1$H-NMR and IR spectra of 5-aza-2,9,13-trioxa-1-sila-1,5-dimethylbicyclo [5.5.1]tridecane in Example 1, respectively.

The notation (Cn-Cm) means a group containing from n to m carbon atoms per group.

One embodiment of the invention is a polycyclic aminosilane compound having the general formula (1).

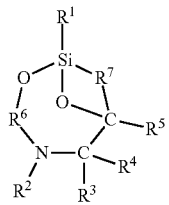

(1)

In formula (1), $R^1$ is a substituted or unsubstituted $C_1$-$C_{20}$, preferably $C_1$-$C_{10}$, more preferably $C_1$-$C_5$, monovalent hydrocarbon group or an organoxy group having the general formula (2):

—$OR^8$ (2)

wherein $R^8$ is a substituted or unsubstituted $C_1$-$C_{20}$, preferably $C_1$-$C_{10}$, more preferably $C_1$-$C_5$, monovalent hydrocarbon group. $R^2$ to $R^5$ are each independently a substituted or unsubstituted $C_1$-$C_{20}$, preferably $C_1$-$C_{10}$, more preferably $C_1$-$C_5$, monovalent hydrocarbon group. $R^6$ and $R^7$ are each independently a substituted or unsubstituted $C_1$-$C_{20}$, preferably $C_1$-$C_{10}$, more preferably $C_1$-$C_5$, divalent hydrocarbon group which may contain a heteroatom.

The substituted or unsubstituted $C_1$-$C_{20}$ monovalent hydrocarbon group, represented by $R^1$ to $R^5$ and $R^8$, may be straight, branched or cyclic. Examples include alkyl, alkenyl, aryl and aralkyl groups, and specifically, straight alkyl groups such as methyl, ethyl, propyl, butyl, pentyl, hexyl, heptyl, octyl, decyl, dodecyl, tetradecyl, hexadecyl, octadecyl and eicosyl; branched alkyl groups such as isopropyl, isobutyl, sec-butyl, tert-butyl, thexyl and 2-ethylhexyl; cyclic alkyl groups such as cyclopentyl and cyclohexyl; alkenyl groups such as vinyl, allyl, butenyl and pentenyl; aryl groups such as phenyl and tolyl; and aralkyl groups such as benzyl. Inter alia, $C_1$-$C_3$ straight alkyl groups such as methyl, ethyl and propyl, and $C_1$-$C_5$ alkenyl groups such as allyl, butenyl and pentenyl are preferred for the availability of reactants and the utility of products.

Also included are substituted forms of the foregoing hydrocarbon groups in which one or more or even all hydrogen atoms are substituted by other substituents. Suitable substituents include $C_1$-$C_3$ alkoxy groups such as methoxy, ethoxy and (iso)propoxy; halogen atoms such as fluorine, chlorine, bromine and iodine; cyano groups, amino groups, $C_2$-$C_{10}$ acyl groups, trichlorosilyl groups, and trialkylsilyl, dialkylmonochlorosilyl, monoalkyldichlorosilyl, trialkoxysilyl, dialkylmonoalkoxysilyl and mono alkyl-dialkoxysilyl groups in which each alkyl or alkoxy moiety has 1 to 5 carbon atoms.

Examples of the optionally heteroatom-containing $C_1$-$C_{20}$ divalent hydrocarbon group, represented by $R^6$ and $R^7$, include alkylene groups such as methylene, ethylene, methylethylene (propylene), trimethylene, methylpropylene, tetramethylene, hexamethylene, octamethylene, decamethylene and isobutylene; arylene groups such as phenylene and methylphenylene; aralkylene groups such as ethylenephenylene and ethylenephenylenemethylene; and oxaalkylene groups such as 2-oxapropylene and 2-oxapentylene. It is preferred for the availability of reactants and the utility of products that $R^6$ be a $C_1$-$C_5$ alkylene group and $R^7$ be a $C_1$-$C_5$ oxaalkylene group.

Examples of the polycyclic aminosilane compound having formula (1) include:

5-aza-2,9,11-trioxa-1-sila-1,5-dimethylbicyclo[5.3.1]undecane, 5-aza-2,9,11-trioxa-1-sila-1-methoxy-5-methylbicyclo [5.3.1]undecane, 5-aza-2,9,11-trioxa-1-sila-1-ethoxy-5-methylbicyclo[5.3.1] undecane, 5-aza-2,9,11-trioxa-1-sila-5-methyl-1-methylbicyclo[5.3.1] undecane, 5-aza-2,9,11-trioxa-1-sila-5-ethyl-1-methoxybicyclo[5.3.1] undecane, 5-aza-2,9,11-trioxa-1-sila-1-ethoxy-5-ethylbicyclo[5.3.1] undecane, 5-aza-2,9,11-trioxa-1-sila-1,3,5-trimethylbicyclo[5.3.1]undecane, 5-aza-2,9,11-trioxa-1-sila-1-methoxy-3,5-dimethylbicyclo [5.3.1]undecane, 5-aza-2,9,11-trioxa-1-sila-1-ethoxy-3,5-dimethylbicyclo [5.3.1]undecane, 5-aza-2,9,11-trioxa-1-sila-5-ethyl-1,3-dimethylbicyclo [5.3.1]undecane, 5-aza-2,9,11-trioxa-1-sila-5-ethyl-1-methoxy-3-methylbicyclo[5.3.1]undecane, 5-aza-2,9,11-trioxa-1-sila-1-ethoxy-5-ethyl-3-methylbicyclo[5.3.1]undecane, 6-aza-2,10,12-trioxa-1-sila-1,6-dimethylbicyclo[6.3.1]dodecane,
6-aza-2,10,12-trioxa-1-sila-1-methoxy-6-methylbicyclo[6.3.1]dodecane,
6-aza-2,10,12-trioxa-1-sila-1-ethoxy-6-methylbicyclo[6.3.1]dodecane,
6-aza-2,10,12-trioxa-1-sila-6-ethyl-1-methylbicyclo[6.3.1]dodecane,
6-aza-2,10,12-trioxa-1-sila-6-ethyl-1-methoxybicyclo[6.3.1]dodecane,
6-aza-2,10,12-trioxa-1-sila-1-ethoxy-6-ethylbicyclo[6.3.1]dodecane,
6-aza-2,10,12-trioxa-1-sila-1,3,6-trimethylbicyclo[6.3.1]dodecane,
6-aza-2,10,12-trioxa-1-sila-1-methoxy-3,6-dimethylbicyclo[6.3.1]dodecane,
6-aza-2,10,12-trioxa-1-sila-1-ethoxy-3,6-dimethylbicyclo[6.3.1]dodecane,
6-aza-2,10,12-trioxa-1-sila-6-ethyl-1,3-dimethylbicyclo[6.3.1]dodecane,
6-aza-2,10,12-trioxa-1-sila-6-ethyl-1-methoxy-3-methylbicyclo[6.3.1]dodecane,
6-aza-2,10,12-trioxa-1-sila-1-ethoxy-6-ethyl-3-methylbicyclo[6.3.1]dodecane,
5-aza-2,9,13-trioxa-1-sila-1,5-dimethylbicyclo[5.5.1]tridecane,
5-aza-2,9,13-trioxa-1-sila-1-methoxy-5-methylbicyclo[5.5.1]tridecane,
5-aza-2,9,13-trioxa-1-sila-1-ethoxy-5-methylbicyclo[5.5.1]tridecane,
5-aza-2,9,13-trioxa-1-sila-5-ethyl-1-methylbicyclo[5.5.1]tridecane,
5-aza-2,9,13-trioxa-1-sila-5-ethyl-1-methoxybicyclo[5.5.1]tridecane,
5-aza-2,9,13-trioxa-1-sila-1-ethoxy-5-ethylbicyclo[5.5.1]tridecane,
5-aza-2,9,13-trioxa-1-sila-5-(N,N-dimethylamino)ethyl-1-methylbicyclo[5.5.1]tridecane,
5-aza-2,9,13-trioxa-1-sila-5-(N,N-dimethylamino)ethyl-1-methoxybicyclo[5.5.1]tridecane,
5-aza-2,9,13-trioxa-1-sila-1-ethoxy-5-(N,N-dimethylamino)ethylbicyclo[5.5.1]tridecane,
5-aza-2,9,13-trioxa-1-sila-5-(N,N-diethylamino)ethyl-1-methylbicyclo[5.5.1]tridecane,
5-aza-2,9,13-trioxa-1-sila-5-(N,N-diethylamino)ethyl-1-methoxybicyclo[5.5.1]tridecane,
5-aza-2,9,13-trioxa-1-sila-1-ethoxy-5-(N,N-diethylamino)ethylbicyclo[5.5.1]tridecane,
5-aza-2,9,13-trioxa-1-sila-1,3,5-trimethylbicyclo[5.5.1]tridecane,
5-aza-2,9,13-trioxa-1-sila-1-methoxy-3,5-dimethylbicyclo[5.5.1]tridecane,
5-aza-2,9,13-trioxa-1-sila-1-ethoxy-3,5-dimethylbicyclo[5.5.1]tridecane,
5-aza-2,9,13-trioxa-1-sila-5-ethyl-1,3-dimethylbicyclo[5.5.1]tridecane,
5-aza-2,9,13-trioxa-1-sila-5-ethyl-1-methoxy-3-methylbicyclo[5.5.1]tridecane,
5-aza-2,9,13-trioxa-1-sila-1-ethoxy-5-ethyl-3-methylbicyclo[5.5.1]tridecane,
5-aza-2,9,13-trioxa-1-sila-5-(N,N-dimethylamino)ethyl-1,3-dimethylbicyclo[5.5.1]tridecane,
5-aza-2,9,13-trioxa-1-sila-5-(N,N-dimethylamino)ethyl-1-methoxy-3-methylbicyclo-[5.5.1]tridecane,
5-aza-2,9,13-trioxa-1-sila-1-ethoxy-5-(N,N-dimethylamino)ethyl-3-methylbicyclo-[5.5.1]tridecane,
5-aza-2,9,13-trioxa-1-sila-5-(N,N-diethylamino)ethyl-1,3-dimethylbicyclo[5.5.1]tridecane,
5-aza-2,9,13-trioxa-1-sila-5-(N,N-diethylamino)ethyl-1-methoxy-3-methylbicyclo-[5.5.1]tridecane,
5-aza-2,9,13-trioxa-1-sila-1-ethoxy-5-(N,N-diethylamino)ethyl-3-methylbicyclo-[5.5.1]tridecane,
6-aza-2,10,14-trioxa-1-sila-1,6-dimethylbicyclo[6.5.1]tetradecane,
6-aza-2,10,14-trioxa-1-sila-1-methoxy-6-methylbicyclo[6.5.1]tetradecane,
6-aza-2,10,14-trioxa-1-sila-1-ethoxy-6-methylbicyclo[6.5.1]tetradecane,
6-aza-2,10,14-trioxa-1-sila-6-ethyl-1-methylbicyclo[6.5.1]tetradecane,
6-aza-2,10,14-trioxa-1-sila-6-ethyl-1-methoxybicyclo[6.5.1]tetradecane,
6-aza-2,10,14-trioxa-1-sila-1-ethoxy-6-ethylbicyclo[6.5.1]tetradecane,
6-aza-2,10,14-trioxa-1-sila-6-(N,N-dimethylamino)ethyl-1-methylbicyclo[6.5.1]tetradecane,
6-aza-2,10,14-trioxa-1-sila-6-(N,N-dimethylamino)ethyl-1-methoxybicyclo[6.5.1]tetradecane,
6-aza-2,10,14-trioxa-1-sila-1-ethoxy-6-(N,N-dimethylamino)ethylbicyclo[6.5.1]tetradecane,
6-aza-2,10,14-trioxa-1-sila-6-(N,N-diethylamino)ethyl-1-methylbicyclo[6.5.1]tetradecane,
6-aza-2,10,14-trioxa-1-sila-6-(N,N-diethylamino)ethyl-1-methoxybicyclo[6.5.1]tetradecane,
6-aza-2,10,14-trioxa-1-sila-1-ethoxy-6-(N,N-diethylamino)ethylbicyclo[6.5.1]tetradecane,
6-aza-2,10,14-trioxa-1-sila-1,3,6-trimethylbicyclo[6.5.1]tetradecane,
6-aza-2,10,14-trioxa-1-sila-1-methoxy-3,6-dimethylbicyclo[6.5.1]tetradecane,
6-aza-2,10,14-trioxa-1-sila-1-ethoxy-3,6-dimethylbicyclo[6.5.1]tetradecane,
6-aza-2,10,14-trioxa-1-sila-6-ethyl-1,3-dimethylbicyclo[6.5.1]tetradecane,
6-aza-2,10,14-trioxa-1-sila-6-ethyl-1-methoxy-3-methylbicyclo[6.5.1]tetradecane,
6-aza-2,10,14-trioxa-1-sila-1-ethoxy-6-ethyl-3-methylbicyclo[6.5.1]tetradecane,
6-aza-2,10,14-trioxa-1-sila-6-(N,N-dimethylamino)ethyl-1,3-dimethylbicyclo-[6.5.1]tetradecane,
6-aza-2,10,14-trioxa-1-sila-6-(N,N-dimethylamino)ethyl-1-methoxy-3-methylbicyclo-[6.5.1]tetradecane,
6-aza-2,10,14-trioxa-1-sila-1-ethoxy-6-(N,N-dimethylamino)ethyl-3-methylbicyclo-[6.5.1]tetradecane,
6-aza-2,10,14-trioxa-1-sila-6-(N,N-diethylamino)ethyl-1,3-dimethylbicyclo[6.5.1]tetradecane,
6-aza-2,10,14-trioxa-1-sila-6-(N,N-diethylamino)ethyl-1-methoxy-3-methylbicyclo-[6.5.1]tetradecane, and
6-aza-2,10,14-trioxa-1-sila-1-ethoxy-6-(N,N-diethylamino)ethyl-3-methylbicyclo-[6.5.1]tetradecane.

The polycyclic aminosilane compound having formula (1) may be prepared, for example, by a method comprising the steps of reacting an epoxy-containing organoxysilane compound having the general formula (3) with a hydroxyl-containing amine compound having the general formula (4), and distilling the resulting reaction mixture.

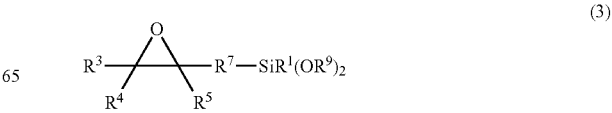

(3)

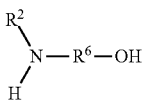
(4)

Herein $R^1$ to $R^7$ are as defined above, $R^9$ is a substituted or unsubstituted $C_1$-$C_{20}$, preferably $C_1$-$C_{10}$, more preferably $C_1$-$C_5$, monovalent hydrocarbon group.

In formula (3), examples of the substituted or unsubstituted $C_1$-$C_{20}$ monovalent hydrocarbon group $R^9$ are as exemplified above for $R^1$.

Examples of the epoxy-containing organoxysilane compound having formula (3) include glycidoxymethyltrimethoxysilane, glycidoxymethyldimethoxymethylsilane, glycidoxymethyltriethoxysilane, glycidoxymethyldiethoxymethylsilane, 3-glycidoxypropyltrimethoxysilane, 3-glycidoxypropyldimethoxymethylsilane, 3-glycidoxypropyltriethoxysilane, and 3-glycidoxypropyldiethoxymethylsilane.

Examples of the hydroxyl-containing amine compound having formula (4) include methylethanolamine, ethylethanolamine, methylisopropanolamine, ethylisopropanolamine, (N,N-dimethylaminoethyl)ethanolamine, (N,N-diethylaminoethyl)ethanolamine, (N,N-dimethylaminoethyl)isopropanolamine, and (N,N-diethylaminoethyl)isopropanolamine.

While the epoxy-containing organoxysilane compound having formula (3) and the hydroxyl-containing amine compound having formula (4) may be mixed in any desired ratio, it is preferred from the standpoints of reactivity and productivity to mix 1 mole of the compound having formula (3) with 0.2 to 5.0 moles, more preferably 0.5 to 2.0 moles of the compound having formula (4).

The reaction may take place either in the presence or absence of a catalyst. A catalyst may be used for the purpose of accelerating the reaction rate. Suitable catalysts include basic catalysts such as sodium hydroxide, potassium hydroxide, sodium methoxide, sodium ethoxide, sodium methoxide in methanol, and sodium ethoxide in ethanol; acid catalysts, for example, sulfonic acids such as methanesulfonic acid, benzenesulfonic acid, toluenesulfonic acid, dodecylbenzenesulfonic acid, and trifluoromethanesulfonic acid, mineral acids such as sulfuric acid, hydrochloric acid and nitric acid, and salts of the foregoing acids. While the catalyst may be used in any desired amount, it is preferred from the standpoints of reactivity and productivity to use 0.0001 to 0.2 mole, more preferably 0.001 to 0.1 mole of the catalyst per mole of the epoxy-containing organoxysilane compound having formula (3).

The reaction may take place either in the presence or absence of a solvent. When used, suitable solvents include hydrocarbon solvents such as pentane, hexane, cyclohexane, heptane, isooctane, benzene, toluene and xylene; ether solvents such as diethyl ether, tetrahydrofuran, and dioxane; ester solvents such as ethyl acetate and butyl acetate; aprotic polar solvents such as acetonitrile, N,N-dimethylformamide and N-methylpyrrolidone; chlorinated hydrocarbon solvents such as dichloromethane and chloroform; alcohol solvents such as methanol, ethanol, 1-propanol and 2-propanol, which may be used alone or in admixture.

The reaction proceeds as shown by the following scheme. First, the epoxy-containing organoxysilane compound having formula (3) reacts with the hydroxyl-containing amine compound having formula (4) to form a hydroxyl-containing aminoorganosilane compound. In the subsequent step of distilling the reaction solution containing the hydroxyl-containing aminoorganoxysilane compound, intramolecular dealcoholization cyclization occurs to form the desired polycyclic aminosilane compound.

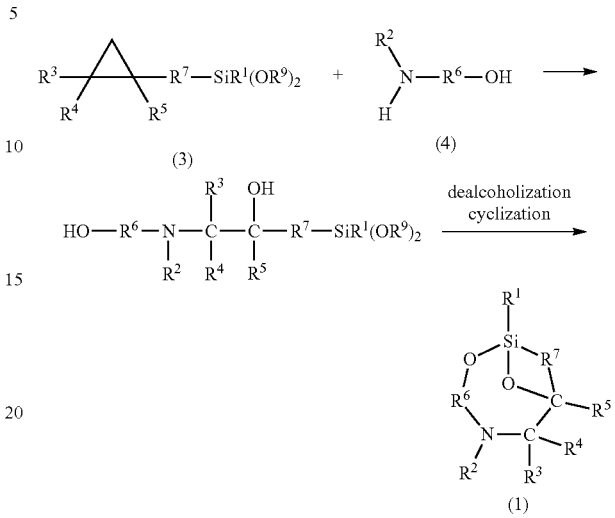

The distillation may be performed by any conventional techniques. Preferably distillation is performed in the presence of a basic or acid catalyst in order to accelerate the rate of dealcoholization reaction, and also for the purpose of cracking a high molecular weight compound resulting from intramolecular dealcoholization cyclization in the reaction solution to convert it to the desired polycyclic aminosilane compound. Sometimes, the reaction solution thickens or even solidifies due to formation of the high molecular weight compound. To avoid this phenomenon, a solvent is preferably added to the reaction solution prior to the distillation. More preferably a solvent having a higher boiling point than the desired polycyclic aminosilane compound is added prior to the distillation.

Examples of the catalyst which is preferably present during distillation include basic catalysts such as sodium hydroxide, potassium hydroxide, sodium methoxide, sodium ethoxide, sodium methoxide in methanol, and sodium ethoxide in ethanol; acid catalysts, for example, sulfonic acids such as methanesulfonic acid, benzenesulfonic acid, toluenesulfonic acid, dodecylbenzenesulfonic acid, and trifluoromethanesulfonic acid, mineral acids such as sulfuric acid, hydrochloric acid and nitric acid, and salts of the foregoing acids. While the catalyst may be used in any desired amount, it is preferred from the standpoints of reactivity and productivity to use 0.0001 to 0.2 mole, more preferably 0.001 to 0.1 mole of the catalyst per mole of the epoxy-containing organoxysilane compound having formula (3).

The solvent which is preferably present during distillation may be selected as appropriate depending on the boiling point of the desired compound. Suitable solvents include hydrocarbon solvents such as pentane, hexane, cyclohexane, heptane, isooctane, decane, tridecane, octadecane, eicosane, benzene, toluene, xylene and dodecylbenzene; ether solvents such as diethyl ether, tetrahydrofuran, dioxane and diphenyl ether; ester solvents such as ethyl acetate, butyl acetate, methyl stearate, and methyl oleate; aprotic polar solvents such as acetonitrile, N,N-dimethylformamide and N-methylpyrrolidone; chlorinated hydrocarbon solvents such as dichloromethane and chloroform; alcohol solvents such as methanol, ethanol, 1-propanol, 2-propanol, 1-decanol, 1-octadecanol, 2-hexyl-1-decanol, oleyl alcohol and 1-docosanol, which may be used alone or in admixture.

EXAMPLE

Examples of the invention are given below by way of illustration and not by way of limitation.

It is noted that $^1$H-NMR spectroscopy uses 600 MHz and deuterated chloroform solvent and IR spectroscopy is by D-ATR.

Example 1

A flask equipped with a stirrer, reflux condenser, dropping funnel and thermometer was charged with 94.6 g (1.3 mol) of methylethanolamine and 76.8 g of methanol and heated at 60° C. After the internal temperature became constant, 264.4 g (1.2 mol) of 3-glycidoxypropyldimethoxymethylsilane was added dropwise over 2 hours, and stirring was continued at the temperature for 2 hours. Afterward 4.6 g of a methanol solution of 28 wt % sodium methoxide and 300 g of 1-octadecanol were added to the reaction solution, which was distilled. There was collected 213.2 g of a fraction at a boiling point 114-116° C./0.4 kPa.

Figure 2:
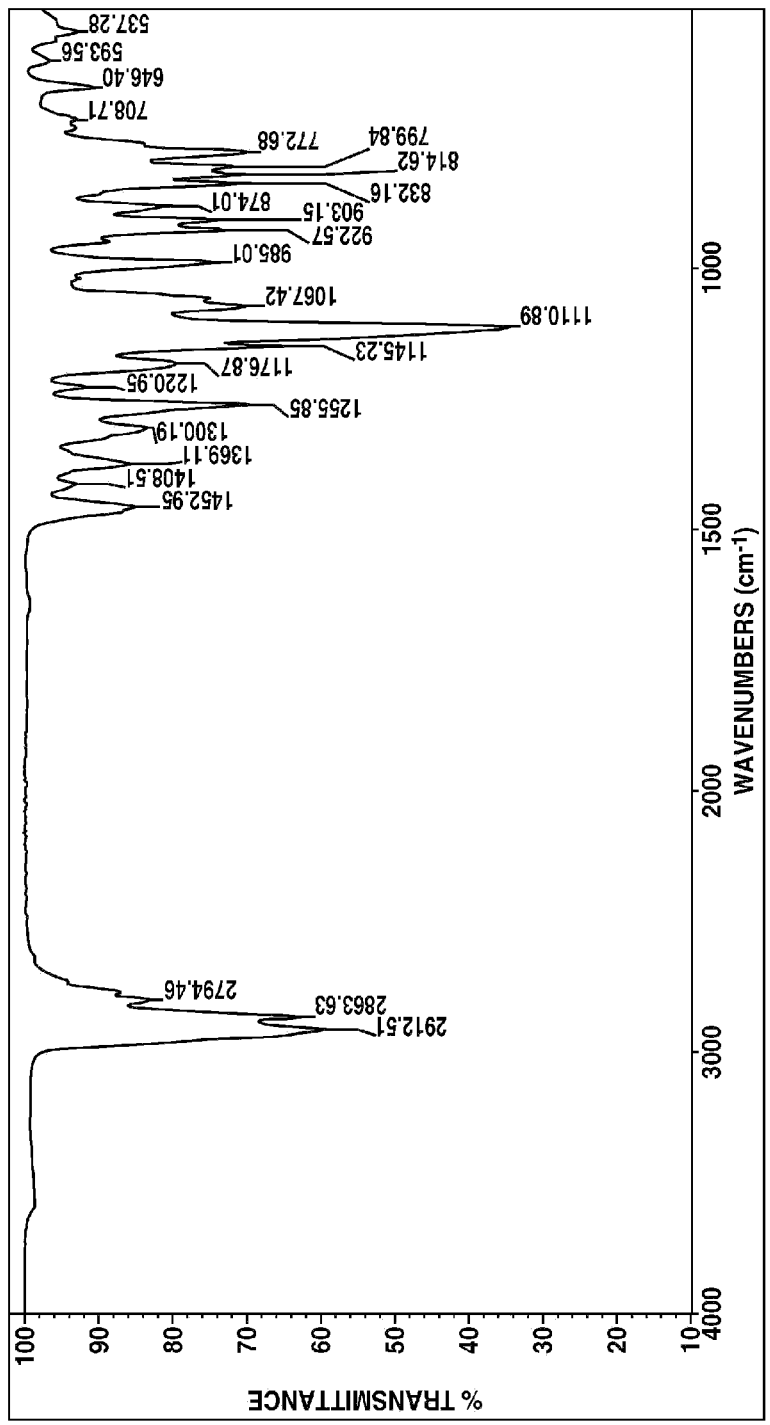

On analysis by mass, $^1$H-NMR and IR spectroscopy, the fraction was identified to be 5-aza-2,9,13-trioxa-1-sila-1,5-dimethylbicyclo[5.5.1]tridecane. FIG. 1 shows $^1$H-NMR spectrum and FIG. 2 shows IR spectrum.

Mass Spectrum m/z 231, 216, 188, 174, 158, 58

Example 2

The reaction and distillation steps in Example 1 were repeated aside from adding 1-octadecane instead of 1-octadecanol prior to distillation. There was collected 205.3 g of a fraction at a boiling point 114-116° C./0.4 kPa. On analysis by mass, $^1$H-NMR and IR spectroscopy, the fraction was found to be identical with Example 1, i.e., 5-aza-2,9,13-trioxa-1-sila-1,5-dimethylbicyclo[5.5.1]tridecane.

Example 3

The reaction and distillation steps in Example 1 were repeated aside from adding oleyl alcohol instead of 1-octadecanol prior to distillation. There was collected 213.5 g of a fraction at a boiling point 114-116° C./0.4 kPa. On analysis by mass, $^1$H-NMR and IR spectroscopy, the fraction was found to be identical with Example 1, i.e., 5-aza-2,9,13-trioxa-1-sila-1,5-dimethylbicyclo[5.5.1]tridecane.

Example 4

The reaction and distillation steps in Example 1 were repeated aside from using 298.1 g of 3-glycidoxypropyldiethoxymethylsilane instead of 264.4 g of 3-glycidoxypropyldimethoxymethylsilane and 110.6 g of ethanol instead of 76.8 g of methanol. There was collected 215.5 g of a fraction at a boiling point 114-116° C./0.4 kPa. On analysis by mass, $^1$H-NMR and IR spectroscopy, the fraction was found to be identical with Example 1, i.e., 5-aza-2,9,13-trioxa-1-sila-1,5-dimethylbicyclo[5.5.1]tridecane.

Example 5

A flask equipped with a stirrer, reflux condenser, dropping funnel and thermometer was charged with 112.3 g (1.3 mol) of ethylethanolamine and 76.8 g of methanol and heated at 60° C. After the internal temperature became constant, 264.4 g (1.2 mol) of 3-glycidoxypropyldimethoxymethylsilane was added dropwise over 2 hours, and stirring was continued at the temperature for 2 hours. Afterward 4.6 g of a methanol solution of 28 wt % sodium methoxide and 300 g of 1-octadecanol were added to the reaction solution, which was distilled. There was collected 248.2 g of a fraction at a boiling point 126-127° C./0.4 kPa.

Figure 3:
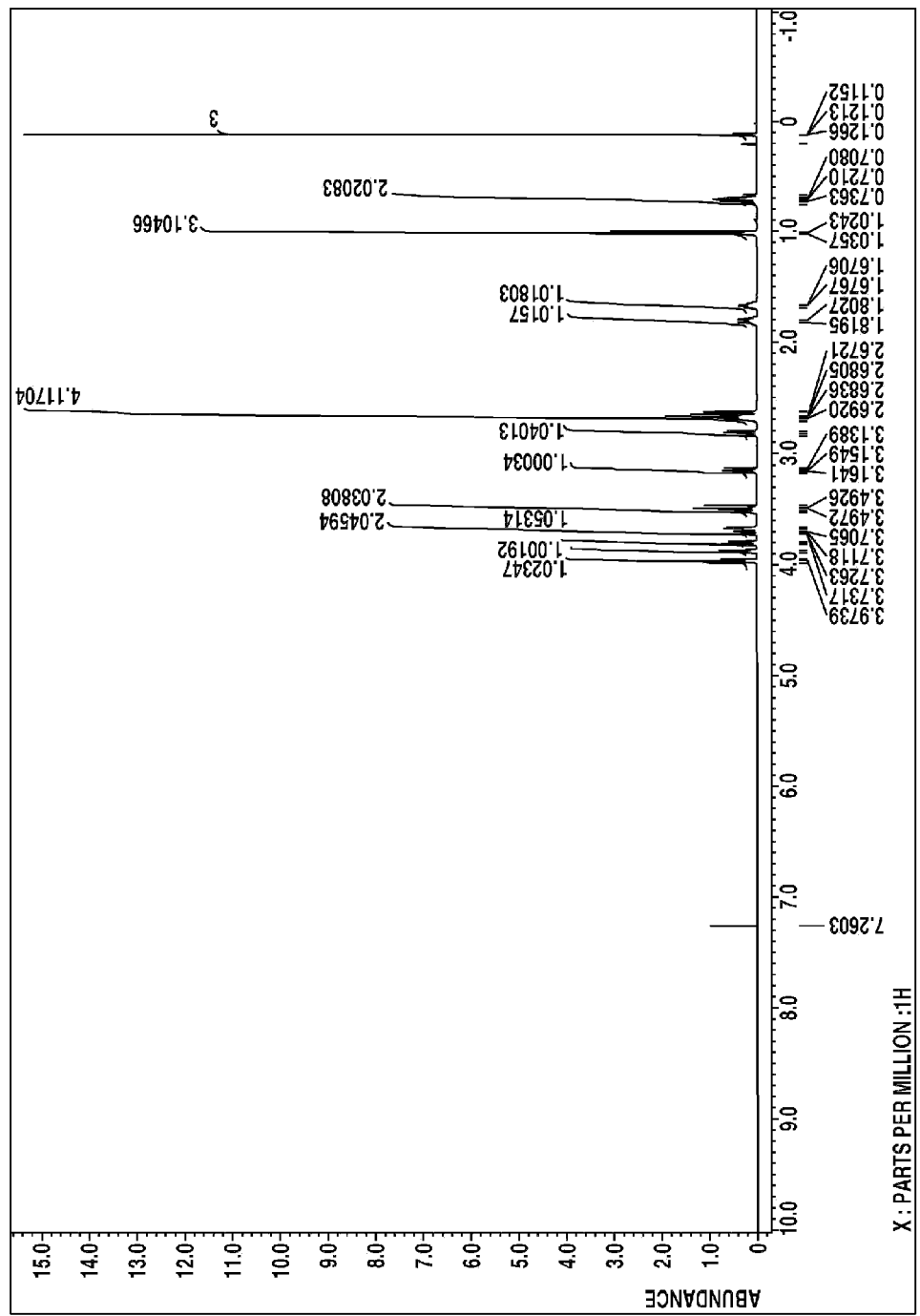
FIGS. 3 and 4 are diagrams showing $^1$H-NMR and IR spectra of 5-aza-2,9,13-trioxa-1-sila-5-ethyl-1-methylbicyclo[5.5.1]tridecane in Example 5, respectively.
Figure 4:
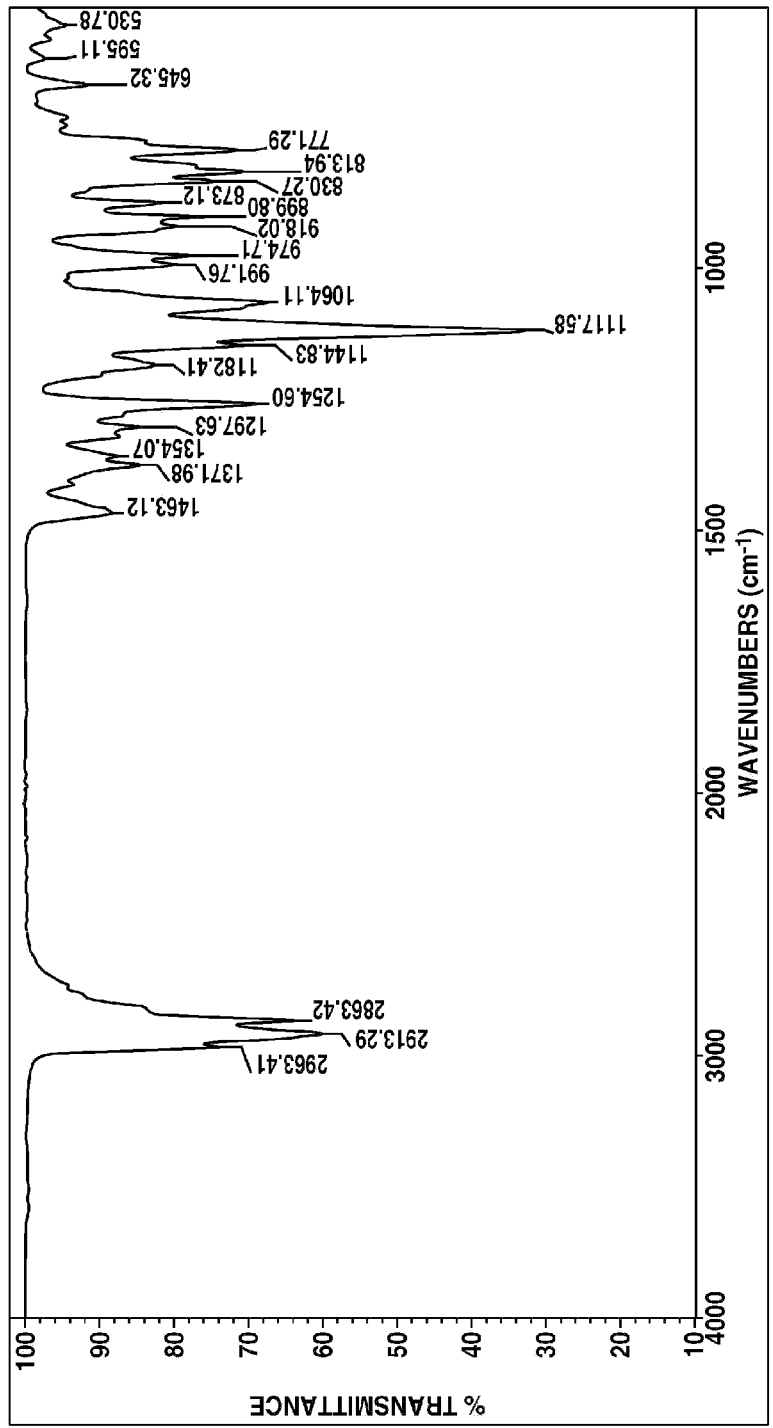

On analysis by mass, $^1$H-NMR and IR spectroscopy, the fraction was identified to be 5-aza-2,9,13-trioxa-1-sila-5-ethyl-1-methylbicyclo[5.5.1]tridecane. FIG. 3 shows $^1$H-NMR spectrum and FIG. 4 shows IR spectrum.

Mass Spectrum m/z 245, 230, 200, 172, 145, 72

Example 6

A flask equipped with a stirrer, reflux condenser, dropping funnel and thermometer was charged with 33.7 g (0.21 mol) of (N,N-diethylaminoethyl)ethanolamine and 12.8 g of methanol and heated at 60° C. After the internal temperature became constant, 44.1 g (0.2 mol) of 3-glycidoxypropyldimethoxymethylsilane was added dropwise over 2 hours, and stirring was continued at the temperature for 2 hours. Afterward 0.77 g of a methanol solution of 28 wt % sodium methoxide and 130 g of 1-docosanol were added to the reaction solution, which was distilled. There was collected 44.2 g of a fraction at a boiling point 141-150° C./0.1 kPa.

Figure 5:
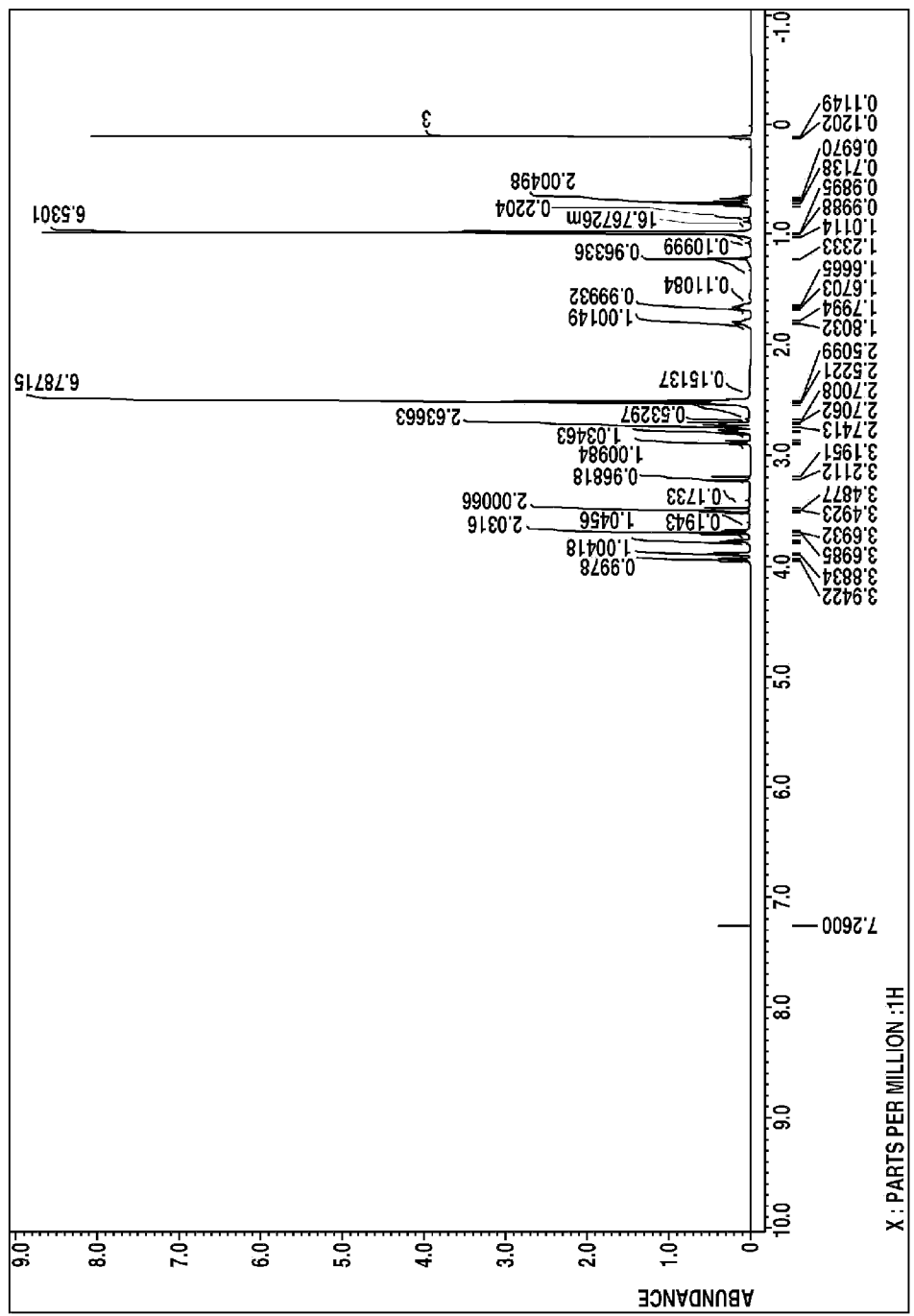
FIGS. 5 and 6 are diagrams showing $^1$H-NMR and IR spectra of 5-aza-2,9,13-trioxa-1-sila-5-(N,N-diethylamino) ethyl-1-methylbicyclo[5.5.1]tridecane in Example 6, respectively.
Figure 6:
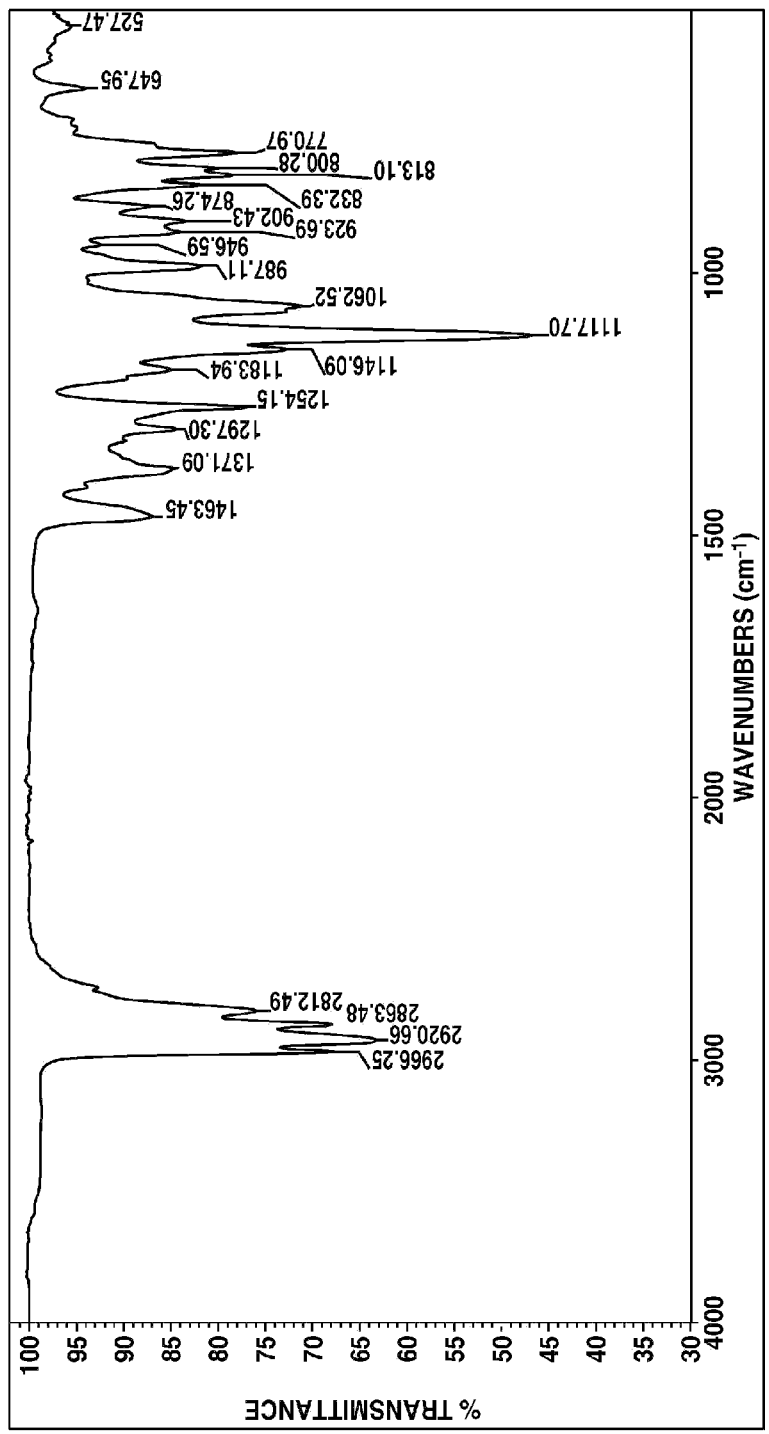

On analysis by mass, $^1$H-NMR and IR spectroscopy, the fraction was identified to be 5-aza-2,9,13-trioxa-1-sila-5-(N,N-diethylamino)ethyl-1-methylbicyclo[5.5.1]tridecane. FIG. 5 shows $^1$H-NMR spectrum and FIG. 6 shows IR spectrum.

Mass Spectrum m/z 230, 143, 101, 100, 86, 58

Japanese Patent Application No. 2017-204952 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polycyclic aminosilane compound having the general formula (1):

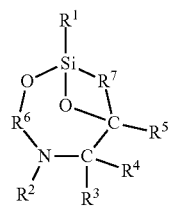

(1)

wherein $R^1$ is a substituted or unsubstituted $C_1$-$C_{20}$ monovalent hydrocarbon group or an organoxy group having the general formula (2):

—$OR^8$ (2)

wherein $R^8$ is a substituted or unsubstituted $C_1$-$C_{20}$ monovalent hydrocarbon group, $R^2$ to $R^5$ are each independently a substituted or unsubstituted $C_1$-$C_{20}$ monovalent hydrocarbon group, $R^6$ and $R^7$ are each independently a substituted or unsubstituted $C_1$-$C_{20}$ divalent hydrocarbon group which may contain a heteroatom.

2. A method for preparing the polycyclic aminosilane compound of claim 1, comprising the steps of:

reacting an epoxy-containing organoxysilane compound having the general formula (3):

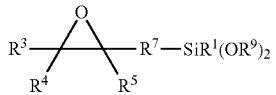

(3)

wherein $R^1$, $R^3$, $R^4$, $R^5$ and $R^7$ are as defined above, $R^9$ is a substituted or unsubstituted $C_1$-$C_{20}$ monovalent hydrocarbon group, with a hydroxyl-containing amine compound having the general formula (4):

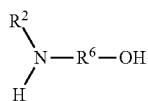

(4)

wherein $R^2$ and $R^6$ are as defined above, and distilling the resulting reaction mixture.

3. The method of claim 2 wherein the distilling step is carried out in the presence of a basic catalyst or acid catalyst.

4. The method of claim 2 wherein in the distilling step, a compound having a higher boiling point than the polycyclic aminosilane compound of formula (1) is used as a solvent.

\* \* \* \* \*